United States Patent [19]

Machida et al.

[11] Patent Number: 4,853,226

[45] Date of Patent: Aug. 1, 1989

[54] SUSTAINED-RELEASE PARTICULATE PREPARATION AND PROCESS FOR PREPARING THE SAME

[75] Inventors: Minoru Machida, Tokyo; Masayuki Arakawa, Shizuoka, both of Japan

[73] Assignee: Chugai Seiyaku Kabushiki Kaisha, Tokyo, Japan

[21] Appl. No.: 105,887

[22] Filed: Oct. 7, 1987

[30] Foreign Application Priority Data

Oct. 7, 1986 [JP] Japan ................. 61-237027

[51] Int. Cl.$^4$ .................... A61F 2/00; A61K 9/50
[52] U.S. Cl. ..................... 424/426; 424/450; 424/499
[58] Field of Search ............... 424/499, 468, 425, 426, 424/450

[56] References Cited

U.S. PATENT DOCUMENTS

| | | | |
|---|---|---|---|
| 4,443,497 | 4/1984 | Samejima et al. | 424/495 X |
| 4,451,452 | 5/1984 | Deibig et al. | 424/78 |
| 4,711,782 | 12/1987 | Okada et al. | 424/455 |
| 4,745,160 | 5/1988 | Churchill et al. | 525/415 |

FOREIGN PATENT DOCUMENTS

| | | |
|---|---|---|
| 0169566 | 1/1986 | European Pat. Off. . |
| 0215126 | 3/1987 | European Pat. Off. . |
| 0220520 | 5/1987 | European Pat. Off. . |
| 33214 | 2/1984 | Japan . |
| 63613 | 4/1986 | Japan . |
| 65816 | 4/1986 | Japan . |

OTHER PUBLICATIONS

Takenaka, et al., Pharm. Tech. Japan, vol. 2, No. 11, pp. 7-15 (1986).
Woodland, et al., J. Med. Chem., vol. 16, No. 8, pp. 897-901 (1973).
Anderson, et al., Contraception, vol. 13, No. 3, pp. 375-385 (1976).
Beck, et al., Fertil. Steril., vol. 31, No. 5, pp. 545-551 (1979).
Yamashita, et al., Jpn. J. Artif. Organs, vol. 15, No. 1, pp. 218-221 (1986).
Hyon, et al., Polymer Preprints Japan, vol. 31, No. 3, p. 547 (1982).
Sanders, et al., J. Controlled Release, vol. 2, pp. 187-195 (1985).
Kwong, et al., J. Controlled Release, vol. 4, pp. 47-62.

Primary Examiner—Thurman K. Page
Attorney, Agent, or Firm—Morgan & Finnegan

[57] ABSTRACT

A sustained-release particulate preparation having a controlled releasing rate of a pharmacologically active agent contained therein in the living body, and a process for preparing the preparation are disclosed. The preparation comprises a polymeric compound which is capable of being degraded in the living body and which is compatible with living tissue, a pharmacologically active agent, and a natural high molecular weight compound of sugar origin or a derivative thereof. The preparation has fine and uniform particle size and can be administered subcutaneously or intramuscularly for obtaining a long-lasting pharmacological activity.

5 Claims, 2 Drawing Sheets

SUSTAINED-RELEASE PARTICULATE PREPARATION AND PROCESS FOR PREPARING THE SAME

FIELD OF THE INVENTION

This invention relates to a sustained-release particulate preparation having a controlled releasing rate of a pharmacologically active agent in the living body, and a process for preparing such a sustained-release particulate preparation.

BACKGROUND OF THE INVENTION

Hitherto, extensive research has been made for the study of a sustained-release preparation for the purpose of controlling the releasing rate of a pharmaceutically active agent in the living body thereby obtaining a long-lasting pharmacological activity. For example, sustained-release particulate preparations, in the form of microspheres or microcapsules using a polymeric material such as polylactic acid, polyglycolic acid, etc. which is capable of being decomposed in the living body and is compatible with living tissues, have been proposed.

However, the above conventional preparations have problems in that the production of fine particles having uniform particle size and shape is difficult, and roughness and heterogenity are sometimes formed on the surface of the particles. Another problem of the conventional preparation is that the production of particles having substantially the same particle size with high reproducibility is very difficult.

The above problems associated with the conventional preparations bring about various disadvantages so that the control of the releasing rate of pharmacologically active agents contained therein, which is the most important requirement for the sustained-release preparation, sometimes becomes difficult. As a result, serious side-effects may be noted due to the rapid releasing rate of the active agent, particularly, when the dose level is increased for obtaining a long-lasting pharmacological effect of the active agent. On the other hand, when the releasing rate is too low, the desired pharmacological effect cannot be achieved thereby adversely affecting the therapeutic effect on the disease to be treated with the sustained-release preparation.

The present inventors conducted extensive studies on the sustained-release preparations in order to overcome the above disadvantages of the conventional preparation, in particular, on the selection of polymeric compounds as a basic component which is capable of being degraded in the living body and which is compatible with living tissue, as well as the particle size of the preparation, and, as a result, found that certain types of polymeric compounds can be preferably used as a basic component of the sustained-release preparation. However, with respect to the particle size, it was found that the desired object cannot be achieved without any break-through since particles tend to be integrated or aggregated with each other during the formation of particles.

With respect to the particle size, Japanese Pharmacopea stipulates the maximum particle size of particles to be used in the injectable preparations. That is, in General Rules of Preparation, Item of Injection, it is stipulated that the particle sizes suspended in the preparation of suspension injectable preparations must be 150 $\mu$m or less, and, hence, a particle size larger than 150 $\mu$m cannot be used for the injectable preparations. For this reason, conventional particles used for suspension injectable preparations must be subjected to a fractionating operation using a sieve for regulating the particle size so as to meet the above regulation of the Japanese Pharmacopea. Apparently, such an operation is time-consuming and expensive since it should be conducted under aseptic and dustfree conditions, and, therefore, an improvement in the production of particulate preparations on an industrial scale has long been desired in the art.

SUMMARY OF THE INVENTION

As a result of further studies for establishing a process for preparing fine particulate preparations having a fine and uniform particle size and keeping chemical and physical stability without employing the fractionating operation for regulating the particle size, the present inventors found that the desired object can be achieved by using a natural high molecular weight compound of sugar origin or a derivative thereof as a medium for the particle formation, and completed the present invention baed on the above finding.

That is, the present invention relates to a sustained-release particulate preparation which comprises a polymeric compound which is capable of being degraded in the living body and is compatible with living tissue, a pharmacologically active agent, and a natural high molecular weight compound of sugar origin or a derivative thereof, and a process for preparing the sustained-release particulate preparation.

An object of the present invention is therefore to provide a sustained-release particulate preparation containing a pharmacologically active agent and having a fine and uniform particle size and keeping chemical and physical stability in an injectable formulation having a controlled releasing rate of the active agent.

Another object of the present invention is to provide a process for preparing such a sustained-release particulate preparation which can be performed easily, without necessity of fractionating regulation of the particle size using a sieve.

DETAILED DESCRIPTION OF THE INVENTION

Figure 1:
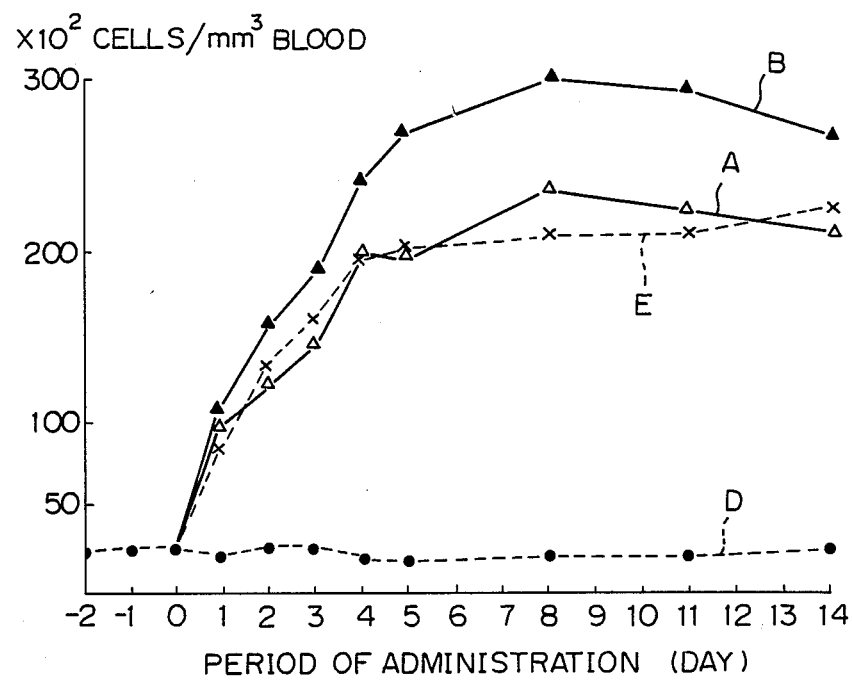
FIGS. 1 and 2 are graphs showing changes in the level of peripheral neutrocytes in blood samples after subcutaneous and intramuscular administrations of the sustained-release particulate preparations containing G-CSF prepared in Examples 1 and 2 of the present invention and the aqueous solution of G-CSF as a control.

The polymeric compound which is capable of being degraded in the living body and which is compatible with living tissue used as one of the components of the sustained-release particulate preparation according to the present invention, is selected from the group consisting of polylactic acid, polyglycolic acid, polyhydroxybutyric acid and a copolymer thereof having a molecular weight of from about 1,000 to about 25,000. The polymeric compound can be used in an amount of from about 20 to about 95% by weight, preferably from 40 to 90% by weight, based on the total weight of the particulate preparation.

The pharmacologically (or physiologically) active agents used in the preparation of the present invention can be any type of active agents which are desirably used as sustained-releasing in the living body, but are preferably those which are water-insoluble or difficulty soluble in water, since it is necessary that a solution of the active agent is suspended in an aqueous solution during the production of the particulate preparation.

Examples of suitable pharmacologically active agents include organic compounds such as ketoprofen, nicorandil, disopyramide, etc., proteins such as interferons, tumor necrosis factor (TNF), colony-stimulating factor, etc. A suitable example of the colony-stimulating factor includes a granular colony stimulating factor (hereinafter referred to as "G-CSF") as disclosed in the applicant's copending Japanese Patent Application Nos. 153273/84, 269455/85, 269456/85, 270838/85, 270839/85 and 166710/86.

These pharmacologically active agents can be used in an amount of from about 0.01 to about 50% by weight based on the total weight of the particulate preparation.

The medium which can be used for the formation of particles and which is one of the essential components of the preparation of this invention is a natural high molecular weight compound of sugar origin or a derivative thereof. Examples of such compounds include at least one member selected from chitins or derivatives thereof, chitosans or derivatives thereof, hyaluronic acid or a salt thereof such as sodium hyalurate, dextrans having a molecular weight of from about 10,000 to about 150,000, pectins, dextrins having a molecular weight of from about 2,500 to about 150,000, and chondroitin sulfate or a salt thereof such as sodium chondroitin sulfate.

The proportion of the medium can be varied suitably depending upon the type of the medium used and/or the dssage form of the particulate preparation so as to provide the final preparation with a desired releasing rate of the active agent. For example, in order to adjust the particle size and surface smoothness of the particles for obtaining a suitable releasing rate, an aqueous solution of the medium having a concentration of from 0.1 to 20% by weight can be used in a proportion of 1 to 20 times (by volume) the solution of the above-described polymeric compound and the pharmacologically active agent.

The sustained-release particulate preparation according to the present invention can be prepared in the following manner.

(1) A polymeric compound which is capable of being decomposed in the living body and is compatible with living tissue is dissolved in an organic solvent.

(2) A pharmacologically active agent is added to the solution prepared in (1) above to form a solution, suspension or emulsion.

(3) An aqueous solution of a medium comprising a natural high molecular weight compound of sugar origin or a derivative thereof is mixed with the solution (or suspension or emulsion) prepared in (2) above, followed by stirring to prepare fine particles containing the pharmacologically active agent.

(4) The fine particles obtained in (3) above are isolated from the mixture to obtain the desired sustained-release fine particulate preparation.

Examples of the organic solvents used above include methyl acetate, ethyl acetate, methyl alcohol, ethyl alcohol, isobutyl alcohol, n-propyl alcohol, isopropyl alcohol, acetone, methylene chloride, toluene, benzene and the like, either alone or as a mixture thereof.

In order to dissolve (or suspend or emulsify) the pharmacologically active agent in the solution of the polymeric compound, it is preferred to use a surface active agent having an HLB (hydrophilic-lipophilic balance) of 8 or less. Examples of the surface active agents having an HLB of 8 or less include at least one of egg yolk lecithin, hydrogenated lecithin, aliphatic acid esters of sorbitan, aliphatic acid esters of polyoxyethylene and aliphatic acid esters of glycerin.

It is necessary that all the above process steps are conducted aseptically.

The sustained-release particulate preparation according to the present invention may contain additional components such as a dispersing agent, a preservative, a pain-alleviating agent, and the like.

The sustained-release particulate preparation according to the present invention can be administered through various routes depending upon the conditions of the disease to be treated, but, generally can be used by subcutaneous or intramuscular injection.

The present invention is further illustrated in more detail by the following examples and test example, but the present invention is not limited thereto. Unless otherwise indicated, all parts, percents, ratios and the like are by weight.

EXAMPLE 1

A poly(dl-lactic acid-glycolic acid) copolymer (75:25) having a molecular weight of about 2,000 was dissolved in 200 ml of a mixture of methylene chloride and n-propanol (4:1 by volume) to prepare a 5% solution of the copolymer. Then, a suspension of 2.5 mg of freeze-dried G-CSF powder in 50 ml of a mixture of methylene chloride and n-propanol (4:1 by volume) was added to the above-prepared methylene chloride-n-propanol solution of the copolymer, and the mixture was stirred and mixed while rotating at a rate of 1,000 rpm with a stirrer to prepare a mixed solution.

The resulting mixed solution was added to 1,000 ml of a 1% aqueous solution of hyaluronic acid which had been kept at 40° C., and the mixture was emulsified while stirring at a rate of 500 rpm to produce microspheres containing G-CSF. The microspheres were collected by centrifugation, repeatedly washed 5 times with distilled water which had been kept at 40° C. and then dried under reduced pressure at room temperature. The G-CSF microspheres obtained in this way was a white powder having an average particle size of 100 μm or below. All the above steps for the preparation were conducted aseptically.

EXAMPLE 2

A poly(dl-lactic acid-hydroxybutyric acid) copolymer (90:10) having a molecular weight of about 2,000 was dissolved in 200 ml of a mixture of toluene and methylene chloride (4:1 by volume) to prepare a 5% solution of the copolymer. Then, a suspension of 2.5 mg of freeze-dried G-CSF powder in 50 ml of a mixture of toluene and methylene chloride (4:1 by volume) was added to the above-prepared toluene-methylene chloride solution of the copolymer, and the mixture was stirred and mixed while rotating at a rate of 1,000 rpm with a stirrer to prepare a mixed solution.

The resulting mixed solution was added to 1,000 ml of a 0.2% aqueous solution of chitin which had been kept at 40° C., and the mixture was emulsified while stirring at a rate of 500 rpm to produce microspheres containing G-CSF. The resulting microspheres were worked up in the same manner as described in Example 1 to obtain a microsphere preparation as a white powder having an average particle size of 100 μm or less. All the above steps for the preparation were conducted aseptically.

EXAMPLE 3

A poly(dl-lactic acid-hydroxybutyric acid) copolymer (90:10) having a molecular weight of about 2,000 was dissolved in 200 ml of methylene chloride to prepare a 5% solution of the copolymer. Then, 50 mg of nicorandil was added to the above methylene chloride solution of the copolymer, and the mixture was stirred and mixed while rotating at a rate of 1,000 rpm with a stirrer.

The resulting mixed solution was added to 1,000 ml of a 0.2% aqueous solution of hyaluronic acid which had been kept at 40° C., and the mixture was emulsified while stirring at a rate of 500 rpm to produce microspheres containing nicorandil. The resulting microspheres were worked up in the same manner as described in Example 1 to obtain a microsphere preparation as a white powder having an average particle size of 100 μm or less. All the above steps for the preparation were conducted aseptically.

EXAMPLE 4

A poly-dl-lactic acid polymer having a molecular weight of about 2,000 was dissolved in 50 ml of a mixture of toluene and acetone (5:1 by volume) to prepare a 10% solution of the polymer. Then, a suspension of 2.5 mg of freeze-dried G-CSF powder in 50 ml of 80% aqueous propanol was added to the above-prepared toluene-acetone solution of the polymer, and the mixture was stirred and mixed while stirring at 1,000 rpm with a stirrer to prepare a mixed solution.

The mixed solution was then added to 500 ml of a 0.5% aqueous chitosan solution which had been warmed at 40° C., and the mixture was emulsified while stirring at a rate of 500 rpm to produce microspheres containing G-CSF. The resulting microspheres were then worked up in the same manner as described in Example 1 to obtain a microsphere preparation containing G-CSF as a white powder having an average particle size of 100 μm or less. All the above steps for the preparation were conducted aseptically.

EXAMPLE 5

A poly-dl-lactic acid polymer having a molecular weight of about 20,000 was dissolved in 50 ml of benzene to prepare a 5% solution of the polymer, and egg yolk lecithin was added to the solution in an amount of 1% concentration. Then, a suspension of 2.5 mg of freeze-dried G-CSF powder in 50 ml of 40% aqueous propanol was added to the above-prepared benzene solution of the polymer, and the mixture was emulsified while stirring and mixing at a rate of 1,000 rpm with a stirrer.

The emulsified mixture was added to a 5% aqueous solution of dextran which had been kept at 40° C., and the mixture was emulsified while stirring at a rate of 500 rpm with a stirrer to produce microspheres containing G-CSF. The resulting microspheres were worked up in the same manner as described in Example 1 to obtain a microsphere preparation containing G-CSF as a white powder having an average particle size of 100 μm or less. All the above steps for the preparation were conducted aseptically.

EXAMPLE 6

A poly(dl-lactic acid-glycolic acid) copolymer (50:50) having a molecular weight of about 6,000 was dissolved in 50 ml of methylene chloride to prepare a 5% solution of the copolymer, and 50 mg of disopyramide was added to the solution. Then, 500 ml of a 1% aqueous pectin solution which had been kept at 40° C. was added to the mixture, and the mixture was emulsified while stirring at a rate of 1,000 rpm with a stirrer. After stirring for 1 hour, methylene chloride was evaporated to produce microspheres containing disopyramide. The resulting microspheres were worked up in the same manner as described in Example 1 to obtain a microsphere preparation containing disopyramide as a white powder having an average particle size of 100 μm or less. All the above steps for the preparation were conducted aseptically.

EXAMPLE 7

A poly(dl-lactic acid-glycolic acid) copolymer (80:20) having a molecular weight of about 2,000 was dissolved in 50 ml of methylene chloride, and egg yolk lecithin was added to the solution in an amount of 1% concentration. Then, a 40% aqueous propanol solution containing G-CSF at a concentration of 50 μg/ml which was prepared by dissolving a G-CSF solution having a concentration of 500 μg/ml in 40% aqueous propanol was added to the above-prepared methylene chloride solution of the copolymer, and the mixture was emulsified while stirring and mixing at a rate of 1,000 rpm with a stirrer. The emulsified mixture was added to 500 ml of a 1% aqueous pectin solution which had been warmed at 40° C., and the mixture was emulsified while stirring at a rate of 500 rpm with a stirrer to produce microspheres containing G-CSF. The resulting microspheres were worked up in the same manner as described in Example 1 to obtain a microsphere preparation containing G-CSF as a white powder having an average particle size of 100 μm or less. All the above steps for the preparation were conducted aseptically.

EXAMPLE 8

A poly-dl-lactic acid polymer having a molecular weight of about 4,000 was dissolved in 50 ml of a mixture of methylene chloride and ethanol to produce a 10% solution of the polymer, and 2.5 mg of freeze-dried α-interferon powder was added to the solution. Then, a 0.5% aqueous chitosan solution which had been warmed at 40° C. was added to the mixture, and the mixture was emulsified while stirring at a rate of 1,000 rpm with a stirrer. After stirring for 1 hour, methylene chloride and ethanol were evaporated to produce microspheres containing α-interferon. The resulting microspheres were worked up in the same manner as described in Example 1 to obtain a microsphere preparation containing α-interferon as a white powder having an average particle size of 100 μm or less. All the above steps for the preparation were conducted aseptically.

EXAMPLE 9

A poly(dl-lactic acid-glycolic acid) copolymer (50:50) having a molecular weight of about 6,000 was dissolved in 50 ml of methylene chloride to prepare a 5% solution of the copolymer, and hydrogenated lecithin was added to the solution in an amount of 1% concentration. Then, a 40% aqueous propanol solution containing G-CSF at a concentration of 50 μg/ml which was prepared by dissolving a G-CSF solution having a concentration of 500 μg/ml in 40% aqueous propanol was added to the above-prepared methylene chloride solution of the copolymer, and the mixture was emulsified while stirring and mixing at a rate of 1,000 rpm with a stirrer. The emulsified mixture was added to 500 ml of a 1% aqueous chitosan solution which had been warmed at 40° C., and the mixture was emulsified while stirring at a rate of 500 rpm to produce microspheres containing G-CSF. The resulting microspheres were worked up in the same manner as described in Example 1 to obtain a microsphere preparation containing G-CSF as a white powder having an average particle size of 100 μm or less. All the above steps for the preparation were conducted aseptically.

Example 10

A poly(glycolic acid-hydroxybutyric acid) copolymer (50:50) having an molecular weight of about 2,000 was dissolved in 50 ml of methylene chloride to prepare a 5% solution of the copolymer, and hydrogenerated lecithin was added to the solution in an amount of 1% concentration. Then, a 70% aqueous propanol solution containing G-CSF at a concentration of 50 μg/ml which was prepared by dissolving a G-CSF solution having a concentration of 500 μg/ml in aqueous propanol was added to the above-prepared methylene chloride solution of the copolymer, and the mixture was emulsified while stirring and mixing at a rate of 1,000 rpm with a stirrer. The emulsified mixture was added to 500 ml of a 1% aqueous sodium hyalurate solution which had been warmed at 40° C., and the mixture was emulsified while stirring at a rate of 500 rpm with a stirrer to produce microspheres containing G-CSF. The resulting microspheres were worked up in the same manner as described in Example 1 to obtain a microsphere preparation containing G-CSF as a white powder having an average particle size of 100 μm or less. All the above steps for the preparation were conducted aseptically.

EXAMPLE 11

A poly-dl-lactic acid polymer having a molecular weight of about 20,000 was dissolved in 50 ml of methylene chloride to prepare a 5% solution of the polymer, and egg yolk lecithin was added to the solution in an amount of 1% concentration. Then, a solution prepared by suspending 2.5 mg of a freeze-dried γ-interferon powder in 50 ml of 40% aqueous propanol was added to the above-prepared methylene chloride solution of the polymer, and the mixture was emulsified while stirring and mixing at a rate of 1,000 rpm with a stirrer. The emulsified mixture was added to 500 ml of a 5% aqueous dextran solution which had been warmed at 40° C., and the mixture was emulsified while stirring at a rate of 500 rpm with a stirrer to produce microspheres containing γ-interferon. The resulting microspheres were worked up in the same manner as described in Example 1 to obtain a microsphere preparation containing γ-interferon as a white powder having an average particle size of 100 μm or less. All the above steps for the preparation were conducted aseptically.

TEST EXAMPLE 1

The effect of the sustained-release particulate preparation containing G-CSF prepared in Examples 1 and 2 above was tested using Wister-Imamichi male rats (13 week-sold). The test was conducted by withdrawing a blood sample for a control at 9 a.m. on the first day, and then administering (1) a physiological saline solution which also contains 0.5% rat serum albumin and a 1% physiological saline solution of mannitol, (2) an aqueous solution of G-CSF as a control, or (3) the sustained-release particulate preparation of Example 1 or 2.

In this experiment, the test sample was administered subcutaneously of intramuscularly in the back-neck site of the rats according to the following schedule. That is, the physiological saline solution was administered in an amount of 0.5 ml/rat once a day for two weeks; the aqueous G-CSF solution was administered in an amount of 0.5 ml/rat (2.5 μg as G-CSF) once a day for two weeks; and each of the G-CSF-containing sustained-release particulate preparations obtained in Examples 1 and 2 was administered in an amount of 0.5 ml/rat (10 μg as G-CSF) at a single dose, followed by evaluating the effect over a period of 2 weeks.

The evaluation of the effect was performed in terms of changes in the number of peripheral neutrocytes as compared with that of the aqueous G-CSF solution as a control. More specifically, an amount of erythrocytes, leukocytes and hemoglobin in the blood sample withdrawn by puncture of the back medial branch of vein was determined using a microcell counter (Toa CC170 Model) and also the hemogram was obtained by a smear preparation of the blood sample. The number of neutrocytes was calculated as a product of the numbers of the leukocytes. The results obtained are shown in the accompanying drawings.

Figure 2:
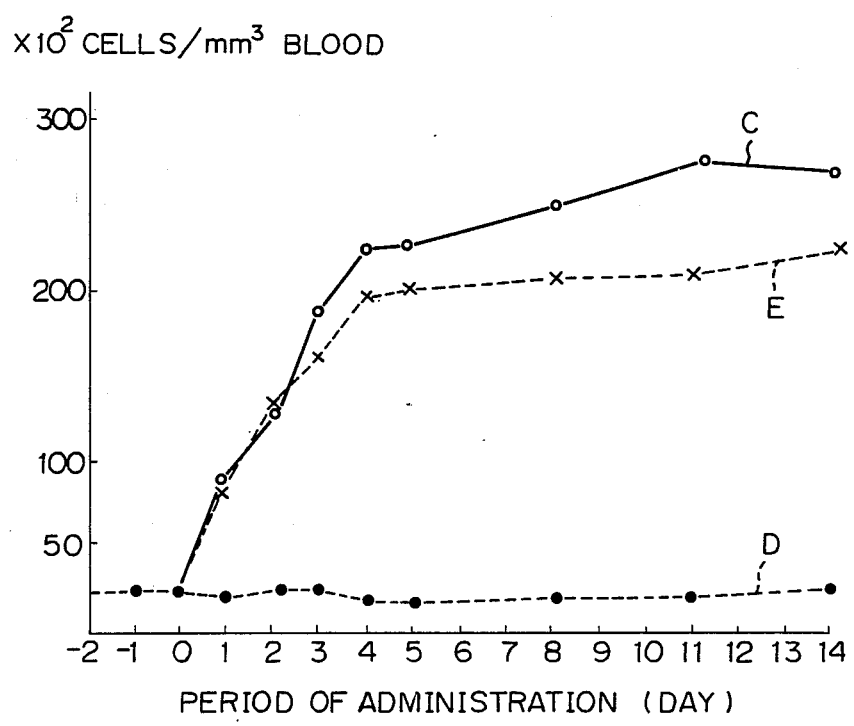

FIGS. 1 and 2 illustrate graphs showing the amount of neutrocytes ($\times 10^2$ cells/mm$^3$ blood) over a period of two weeks obtained by administering the test sample. The graph "A" shows a result obtained by subcutaneous administration of the preparation of Example 1 (10 μg G-CSF/rat/dose); the graph "B" shows the result obtained by intramuscular administration of the preparation of Example 1 (10 μg G-CSF/rat/dose); the graph "C" shows the result obtained by subcutaneous administration of the preparation of Example 2 (10 μg/rat/dose); the graph "D" shows the result obtained by subcutaneous administration of the physiological saline solution (0 μg G-CSF/rat/day); and the graph "E" shows the result obtained by subcutaneous administration of the G-CSF aqueous solution as a control (2.5 μg/rat/day).

The results in FIGS. 1 and 2 clearly demonstrate that the sustained-release particulate preparations according to the present invention exhibit the increase in the number of nutrocytes on every test day after administration to a degree which is substantially equivalent to or higher than that of the control.

As is apparent from the test results, the sustained-release particulate preparation according to the present invention is effective for preventing undesirable hydrolysis of physiologically active agents with enzymes after administration which is often observed in usual injectable preparations, as well as for preventing polymerization of the active agent and the like. Further, the test results indicate that the sustained-release particulate preparation of this invention exhibits an effect substantially equivalent to or even higher than the effect obtained by the control at a lower dose level of the active agent than that of the control.

The sustained-release particulate preparation of the present invention has a structure of microspheres or microcapsules which can be used as an injection or a depo-type preparation, and is excellent in view of their uniformity in grain distribution, fineness of particles and surface smoothness of particles. Accordingly, the sustained-release particulate preparation of this invention is excepted to be useful for the treatment of various diseases since a constant blood level of the physiologically active agent can be maintained after administration of a single dose of the preparation and a long-lasting effect of the active agent can be obtained over a long period of time.

While the invention has been described in detail and with reference to specific embodiments thereof, it will be apparent to one skilled in the art that various changes and modifications can be made therein without departing from the spirit and scope thereof.

What is claimed is:

1. A sustained release particulate preparation consisting essentially of particles having a diameter not greater than 150 micrometers, prepared by a method which comprises the steps of:
   (a) combining an organic solution of a polymeric compound which is capable of being degraded in the living body and is compatible with living tissue, and an organic or organic/aqueous solution of a pharmacologically active agent, which pharmacologically active agent solution is capable of forming a solution, suspension or emulsion with said polymer solution and of forming a suspension in an aqueous solution;
   (b) combining the solution, suspension or emulsion of (a) with an aqueous solution of a natural high molecular weight compound selected from the group consisting of chitins and derivatives thereof, chitosans and derivatives thereof, hyaluronic acid and a salt thereof, soluble dextrans having a molecular weight of from about 10,000 to about 150,000 pectins, dextrins, having a molecular weight of from about 2,500 to about 150,000, and chondroitin sulfate and a salt thereof; and
   (c) recovering said particles therefrom.

2. A sustained-release particulate preparation as claimed in claim 1, wherein said polymeric compound is polylactic acid, polyglycolic acid, polyhydroxybutyric acid or a copolymer thereof.

3. A sustained-release particulate preparation as claimed in claim 1, wherein the pharmacologically active agent-containing solution further comprises a surface active agent having a hydrophilic-lipophilic balance of 8 or less.

4. A sustained-release particulate preparation as claimed in claim 1, wherein said pharmacologically active agent is an organic compound, a protein or a peptide which is water-insoluble or difficulty soluble in water.

5. A method of making a sustained release particulate-preparation consisting essentially of particles having a diameter not greater than 150 micrometers, which method comprises the steps of:
   (a) combining an organic solution of a polymeric compound which is capable of being degraded in the living body and is compatible with living tissue, and an organic or organic/aqueous solution of a pharmacologically active agent, which pharmacologically active agent solution is capable of forming a solution, suspension or emulsion with said polymer solution and of forming a suspension in an aqueous solution;
   (b) combining the solution, suspension or emulsion of (a) with an aqueous solution of a natural high molecular weight compound selected from the group consisting of chitins and derivatives thereof, chitosans and derivatives thereof, hyaluronic acid and a salt thereof, soluble dextrans having a molecular weight of from about 10,000 to about 150,000, pectins, dextrins, hyaving a molecular weight of from about 2,500 to about 150,000, and chondroitin sulfate and a salt thereof; and
   (c) recovering said particles therefrom.

* * * * *